US008047743B2

(12) United States Patent
Simon et al.

(10) Patent No.: US 8,047,743 B2
(45) **Date of Patent: *Nov. 1, 2011**

(54) GEOMORPHOLOGY FOR ENVIRONMENTAL REMEDIATION PROCESS AND SYSTEMS

(75) Inventors: Philip B Simon, Ann Arbor, MI (US); David Richardson, Sheboygan, WI (US); Peter M Simon, Ann Arbor, MI (US)

(73) Assignees: Ann Arbor Technical Services, Ann Arbor, MI (US); Earth-Tech, Sheboygan, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/839,175

(22) Filed: Jul. 19, 2010

(65) Prior Publication Data

US 2011/0081202 A1 Apr. 7, 2011

Related U.S. Application Data

(60) Continuation of application No. 12/043,294, filed on Mar. 6, 2008, now Pat. No. 7,758,283, which is a division of application No. 11/090,538, filed on Mar. 25, 2005, now Pat. No. 7,344,337.

(60) Provisional application No. 60/556,544, filed on Mar. 26, 2004.

(51) Int. Cl.
*B09C 1/00* (2006.01)

(52) U.S. Cl. .................................................... 405/128.1

(58) Field of Classification Search ................ 405/128.1
See application file for complete search history.

(56) References Cited

U.S. PATENT DOCUMENTS

| | | | | |
|---|---|---|---|---|
| 5,053,778 | A | 10/1991 | Imhoff | |
| 5,279,151 | A | 1/1994 | Coody et al. | |
| 5,913,179 | A | 6/1999 | Sutton et al. | |
| 5,951,457 | A | 9/1999 | James | |
| 6,020,185 | A | 2/2000 | Hince et al. | |
| 6,350,383 | B1 | 2/2002 | Douglas | |
| 6,640,470 | B2 | 11/2003 | Chesner et al. | |
| 6,805,798 | B2 | 10/2004 | Kerfoot | |
| 7,011,749 | B2 | 3/2006 | Hayes et al. | |
| 7,344,337 | B2 * | 3/2008 | Simon et al. | 405/128.15 |
| 7,758,283 | B2 * | 7/2010 | Simon et al. | 405/128.1 |

(Continued)

FOREIGN PATENT DOCUMENTS

JP H06-27014 A 2/1994

(Continued)

OTHER PUBLICATIONS

Crave A et al: "A stochastic "precipiton" model for simulating erosion/sedimentation dynamics" Computers & Geosciences Elsevier UK, vol. 27, No. 7, Aug. 2001.

(Continued)

*Primary Examiner* — John Kreck

(74) *Attorney, Agent, or Firm* — Simmons Perrine Moyer Bergman PLC

(57) ABSTRACT

The present invention includes methods for investigating a site for possible selective removal of sediment containing a contaminant. The methods include calculating an adjusted contaminant concentration for sediment zones on the site. The site preferably contains a water course. The methods may also include determining whether sediment zone need remediation by comparing the adjusted contaminant concentration to a standard. The invention also includes a system for carrying out the described methods, at least partially implemented in a computer.

20 Claims, 2 Drawing Sheets

U.S. PATENT DOCUMENTS

| | | | |
|---|---|---|---|
| 7,887,259 B2 * | 2/2011 | Simon et al. | 405/128.1 |
| 2002/0151241 A1 | 10/2002 | Sheahan et al. | |
| 2004/0215428 A1 | 10/2004 | Bras et al. | |
| 2005/0091009 A1 | 4/2005 | Belcher et al. | |
| 2005/0226688 A1 | 10/2005 | Simon et al. | |
| 2006/0027505 A1 | 2/2006 | Hayes et al. | |
| 2006/0122794 A1 | 6/2006 | Sprague et al. | |

FOREIGN PATENT DOCUMENTS

| | | |
|---|---|---|
| JP | 2000-246230 A | 9/2000 |
| JP | 2003-94036 A | 4/2003 |

OTHER PUBLICATIONS

Miller Jerry R: "Role of fluvial geomorphic processes in the dispersal of heavy metals from mine sites" J Geochem Explor; Journal of Geochemical Exploration Apr. 1997 Elsevier Sci B.V., Amsterdam, Netherlands, vol. 58, No. 2-3, Sep. 18, 1995.

Mossa J: "Sediment dynamics in the lowermost Mississippi River" Engineering Geology, Elsevier Science Publishers, Amsterdam, NL, vol. 45, No. 1, Dec. 30, 1996.

Mossa J et al: "Thalweg variability at bridges along a large karst river: the Suwannee River, Florida" Engineering Geology, Elsevier Science Publishers, Amsterdam, NL, vol. 49, No. 1, Feb. 26,1998.

International Search Report dated Jul. 28, 2005, International Application No. PCT/US2005/009907.

U.S. Geological Survey, Toxic Substances Hydrology Program, Toxics Program Remediation Activities, Toxic Substances Hydrology, Lake Coeur d'Alene Remediation Assessment, from http://toxics.usgs.gov/topics/rem__act/coeurdalene__remediation.html, 3 p + 1 p date verification by http://web.archive.org.

Kuwabara, J.S., Berelson, W.M., Balistrieri, L.S., Woods, P.F., Topping, B.R., Steding, D.J., and Krabbenhoft, D.P., 2000, Benthic flux of metals and nutrients into the water column of Lake Coeur d'Alene, Idaho—Repost of Aug. 1999, pilot study: U.S. Geological Survey Water-Resources Investigations Report 00/4132, 74 p.

Summary of the Remediation Technologies Development Forum, Sediments Remediation Action Team, Assessment Subgroup Meeting notes, Sep. 12, 2000, downloaded from http://www.rtdf.org/PUBLIC/sediment/minutes/assess091200.htm; 16 pages.

US EPA, Contaminated Sediments Action Plan, downloaded from http://www.deq.state.mi.us/documents/deq-erd-kzoo-Contaminated-Sediment-Action-Plan.pdf, Jun. 2002, 8 pages.

US EPA, "EPA906-D-98-001 Interim Final RCRA Delisting Technical Support Document", Aug. 1, 2000; download from http://www.epa.gov/arkansas/6pd/rcra__c/pd-o/dtsd.htm; 208 pages plus appenices 2-5 and user guide. Note: Appendices 1a and 1b (Appendix A-1) are not provided, as exceeding 500 pages.

S E Apitz, J W Davis, K Finkelstein, D L Hohreiter, R Hoke, R H Jensen, J M Jersak, V J Kirtay, E E Mack, V Magar, D Moore, D Reible and R Stahl, Critical Issues for Contaminated Sediment Management, MESO-02-TM-01, Mar. 1, 2002, downloaded from http http://meso.spawar.navy.mil/docs/MESO-02-TM-01.pdf, 88 pages.

Sharpley et al, "Assessing Site Vulnerability to Phosphorus Loss in an Agricultural Watershed" downloaded from http://jeq.scijournals.org/cgi/reprint/30/6/2026.pdf; J. Environ. Qual., vol. 30, Nov.-Dec. 2001, 11 pages.

Kyshakevych et al., Monogahela and Youghiogheny Rivers, Pools 2 and Riverbank Geology, Conditions, and Access Reports, 2002, Camegie Mellon University, 33 pages.

* cited by examiner

GEOMORPHOLOGY FOR ENVIRONMENTAL REMEDIATION PROCESS AND SYSTEMS

CLAIM OF PRIORITY

The present application is a continuation of U.S. patent application Ser. No. 12/043,294, filed on Mar. 6, 2008, now U.S. Pat. No. 7,758,283, issued on Jul. 20, 2010, which is a divisional of U.S. patent application Ser. No. 11/090,538, filed on Mar. 25, 2005, now U.S. Pat. No. 7,344,337, issued on Mar. 18, 2008, which turn claims the benefit of U.S. Patent Application 60/556,544, filed on Mar. 26, 2004, all of which are incorporated by reference.

FIELD OF THE INVENTION

The present invention relates generally the area of remediation of contaminated sediment, and more specifically to processes and systems related to investigation and remediation based on the geomorphology of the site to be remediated.

BACKGROUND OF THE INVENTION

Environmental remediation of water bodies often is an extremely expensive and time consuming process of removing contaminated sediment. Numerous problems exist with traditional techniques. Historically, a dredge or excavation approach has been used to remove all the sediment in a remediation site. Such approaches, while ultimately effective, have two main drawbacks.

First is over-removal of sediment. As well as highly contaminated sediment, relatively uncontaminated sediment will also be removed. Because the dredged or excavated sediment must all be treated as if it were contaminated, the over-removal of sediment leads to increased costs of disposal. Since sediment disposal is one of the major costs of remediation, limiting the amount of sediment removed is desirable.

Second is habitat destruction. The dredge or excavation approach is a rather inexact tool, leading to significant destruction of the physical features and natural habitat in the area that has been remediated. This is particularly true for water courses such as streams, rivers, ponds and lakes. Dredging or excavating may be compared to strip mining where entire areas are scoured bare to capture all the contaminated sediment.

The present invention overcomes one or more of these problems.

SUMMARY OF THE INVENTION

The present invention includes methods for investigating a site for possible selective removal of sediment containing a contaminant. The methods include calculating an adjusted contaminant concentration for sediment zones on the site. The site preferably contains a water course. The methods may also include determining whether sediment zone need remediation by comparing the adjusted contaminant concentration to a standard. The invention also includes a system for carrying out the described methods, at least partially implemented in a computer.

DETAILED DESCRIPTION

Figure 1:
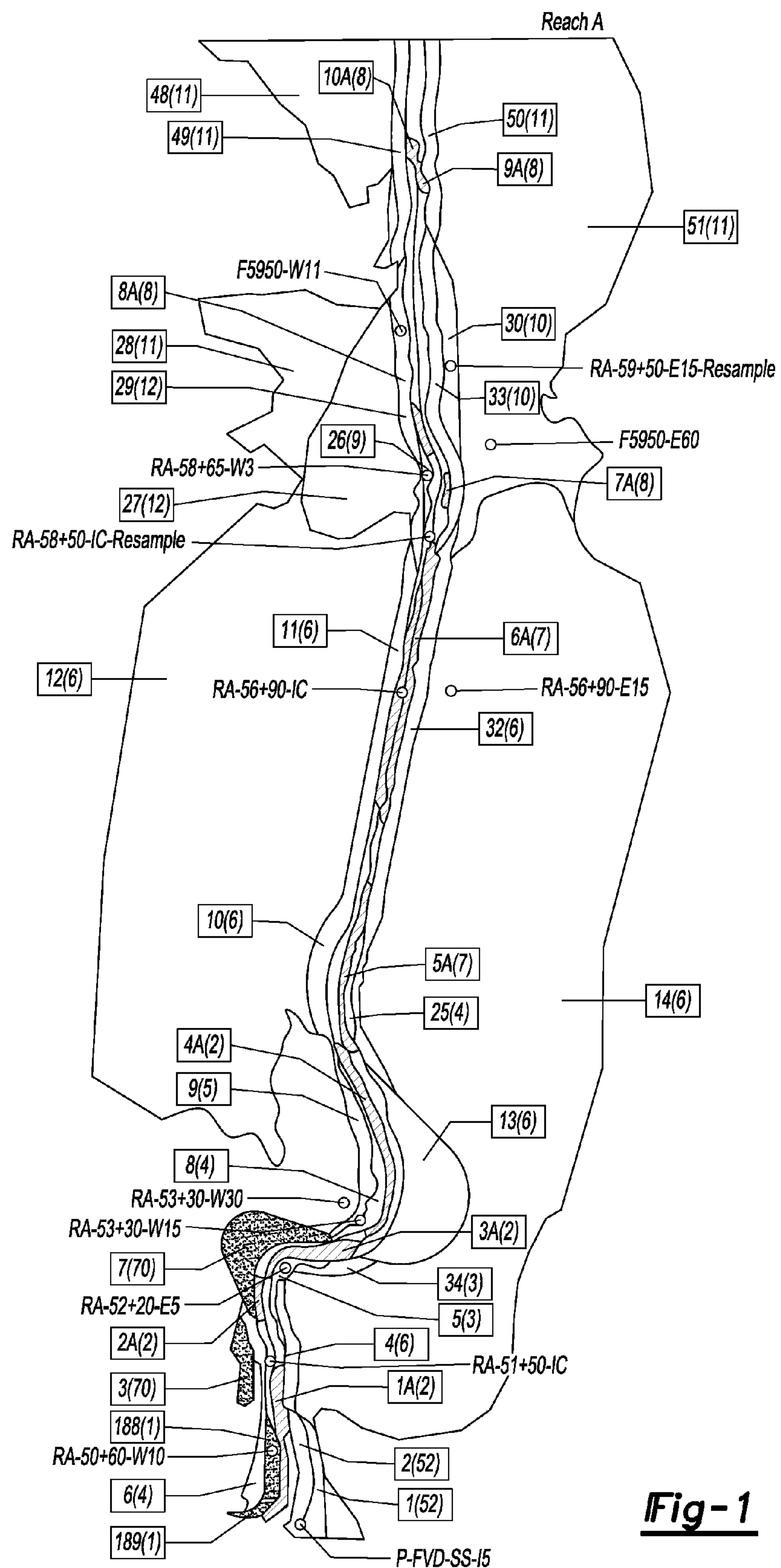
FIG. 1 depicts a remediation site in which adjusted contaminant concentrations have been calculated.

The present invention comprises methods that help minimize the amount of contaminated sediment that must be removed during remediation of a water course and surrounding area, while also adequately removing the contaminant from the site. Selective removal of sediment reduces the cost of remediation while also minimizing the impact of remediation on the natural environment.

After ongoing contamination has been eliminated, remediation of a water course can begin. Remediation is generally designed to remove contaminant from the water course itself while also ensuring that the water course does not become re-contaminated in the future. To meet these dual goals, the methods of the present invention comprise identifying sediment zones along a water course that are in need of remediation. A sediment zone may be in need of remediation because it contains an unacceptable level of contaminant in the water course (e.g. in-channel, on the banks, on the overbanks, or the like). A sediment zone may also be in need of remediation because it contains contaminant that is likely to be reintroduced into the water course at a future time.

The identification of sediment zones may include determining where sediment is deposited and where sediment is eroded within the water course of interest. Geomorphological principals may be used to identify both deposition and erosion zones of the water course. "Applied River Morphology" by Dave Rosgen provides a basic background in geomorphology. This text is incorporated by reference in its entirety. In one embodiment, identification of deposition and erosion zones includes comparing images of the water course at differing points in time; preferably several images are compared that have been captured over a number of years (e.g. 5-20 years between the images). More preferably, the images are digital images or digitized images so as to facilitate use with a computer. Aerial images are preferred as giving large scale context to the water course.

Preferably the comparison of aerial photograph allows the determination of how the water course has changed over the period of ongoing contamination. For example, streams and rivers meander over time due to channel bed armoring and lateral movement or due to flooding which creates a preferred flow pattern. Such changes to the water course may be important to identifying deposition and erosion zones of the water course. Sediment that is not now near the flow channel of the course water may have been so at one time, meaning that a former deposition zone may be remote from current deposition zones.

In addition to using images, topographical data (e.g. maps) of the water course and surrounding area are preferably used in identifying the sediment zones. For example, the gradient of the channel may determine whether it is in a deposition zone or an erosion zone. Other data and data collection techniques may also be used to assist in identifying the sediment zones, such as visual inspections of the water course, identifying the type of sediment in the channel of the water course, and soil profile descriptions. Soil horizon development is similar for geomorphic surfaces that have been subjected to similar parameters such as flooding, scouring, or deposition. Taken to together, the collected information may be mapped to give an output (e.g., a map, graph or chart, or the like) that sets forth the deposition and erosion zones. The output of the identification may be in the form of a tangible media (e.g. paper) or intangible media (e.g. computer readable media) or as information sent to the remediation site (e.g. mapping coordinates to be used by a GPS receiver).

One result of identifying deposition and erosion zones of the water course is the ability to limit the amount of sample testing that needs to be conducted. By understanding where sediment is eroded and deposited, testing may be limited to sediment likely to contain contaminant. Fewer test samples are used due to the understanding of the water course depositional environment. The focus on depositional areas equates to a reduction in the cost of the investigation and the remediation. For example, testing may not be necessary for an erosion zone because any contaminant there will likely have been washed downstream.

Another result of identifying deposition and erosion zones is the ability to identify sediment that may be eroded in the future. Future erosion may lead to reintroduction of the contaminant into the water course.

The identification of sediment zones may include calculating an adjusted concentration of contaminant for each sediment zone. The adjusted concentration of a particular zone incorporates a number of factors including a known or estimated concentration of contaminant (measured in ppm), the area of the zone in square feet, an erosion factor, and a risk attenuation factor.

The concentration of contaminant in a zone may be known by sample testing the sediment of interest. Alternately, the concentration of contaminant in a zone may be estimated. One estimation technique involves the use of a proxy. The known concentration of a contaminant in a proxy zone is assigned to the estimated zone based on similar sediment type, similar relationship to the water course (e.g. in-channel, bank or over bank), similar location with the water course (e.g. proximity to bends and meanders, channel gradient, channel width, etc.). Soft sediment is unconsolidated inorganic/organic material that has settled out of the water course, deposited in the water course, and is easily transportable in the water course under bankfull or flood stage discharge conditions. Non-soft sediment is consolidated inorganic/organic material that is present on the channel bed and is not easily transportable in the water course under bankfull or flood stage discharge conditions. In one preferred embodiment, an estimated concentration of 0.5 ppm may be used for in-channel, non-soft sediments zones, while an estimated concentration of 0.05 ppm may be used for channel bed of bedrock or boulders and cobble. The use of estimated or proxy concentrations is preferred because the technique reduces the amount of sampling that is required.

The erosion factor quantifies the likelihood that sediment will be reintroduced to the water course at some future date. A high erosion factor indicates that the sediment is in the channel of the water course or highly likely to come in contact with water, thus increasing the risk of re-contaminating the water course. On the other hand, a low erosion factor indicates a lower chance that the sediment will be reintroduced into the water in the future.

Assigning the erosion factor takes into account the geomorphology of the water course in question. For water contact areas and areas on the outside of relatively sharp bends, an erosion factor of 1 (high) is used. These areas have the highest erosion factor due to the erosive nature of the thalweg of the water course. The thalweg is the portion of the water course that has the highest velocity and in straight reaches is located in the middle of the water course. In a bend, the thalweg is pushed to the outside of bend, causing the most erosion on the outside of the bend.

For bends that are more gradual, an erosion factor of 0.5 (medium) is used because the full force of the thalweg is not applied against the outside of the bend. An erosion factor of 0.25 (low) is used on banks, the inside of bends and on the overbanks of fairly straight reaches of the water course; some risk of erosion of these areas is present during flood stage. Even though the inside of a bend is usually a deposition zone, it is included here to be conservative. Lastly, areas remote from the water course and areas protected (e.g., boulders, cribbing, revetment, rip-rap, gabions, or the like) in a water course are given an erosion factor of 0.01 (very low). Further reduced erosion factor may also be used for certain bank areas, such as those protected by boulders, cribbing, revetment, rip-rap, gabions, other techniques.

Another factor taken into account in the adjusted concentration is the risk attenuation factor. Remediation activities may skew the tested or estimated concentration of contaminant in a given sediment zone. This is particularly true for sediment zones in the overbank area that are at risk for reintroducing contaminant into the water course after remediation.

Ideally, only clean materials are used to cover contaminated sediment, thus giving a contaminant concentration of zero. However, to be conservative, the risk attenuation factor is applied as follows. If less than two inches of soil cover or rip-rap was used, then an attenuation factor of 1 (no attenuation) may be applied; meaning that the soil cover is deemed to provides no attenuation in the risk of re-introduction. If two to six inches of soil cover or rip-rap was used, a risk attenuation factor of 0.5 (low attenuation) may be applied, meaning that the risk of re-introduction has been halved. If more than 6 inches of soil cover or rip-rap was used, a risk attenuation factor of 0.1 (medium attenuation) may be applied. If more than six inches of cover soil or rip-rap is used in combination with a geotextile, than an attenuation factor of 0.01 (high attenuation) may be applied. For example, permanent roads constructed to access the remediation site may utilize clean soil and/or geotextiles and thus attenuate the risk of reintroduction by a significant degree (e.g., 0.01).

An exemplary adjusted concentration for a sediment zone is as follows. A sample taken from a zone in the channel of the water course was tested to have a concentration 1.2 ppm. Because the zone was in the channel an erosion factor of one (high) was applied. Likewise, no cover soil was used in this zone so a risk attenuation factor of one was also applied. In this instance, the adjusted concentration is the same as the starting concentration. In another example, a sample taken from an uncovered zone in the overbank with an initial concentration of 2.6 ppm has an adjusted concentration of 0.026 ppm because the erosion factor is 0.1, while the risk attenuation factor is 0.1.

As can been seen, the adjusted concentration calculation takes into account the deposition and erosion characteristics of the water course in quantifying the effective amount of contaminant in the sediment. Normalizing and comparing the adjusted concentration to the applicable standard (e.g. site specific requirements, municipal, state or federal laws, regulations, rules or the like) may be used to determine whether a sediment zone needs to be remediated or has been sufficiently remediated.

Identification of sediment zones may also include calculating the area-concentration of each zone from the adjusted concentration and the area, in square feet, of each sediment zone. The area of the sediment zone may be obtained using a Thiessen's polygon approach. The area-concentration quantifies that amount of contaminant at the surface of the sediment zone and gives an overall amount of contaminant in the sediment zone.

The calculation of the area-concentration is summarized in the following formula:

$C \times EF \times RAF \times A = PA$, where

C=tested or estimated concentration,

EF=erosion factor,

RAF=risk attenuation factor,

A=area of the sediment zone (sq. ft.), and

PA=area-concentration (ppm*sq. ft.).

The area-concentration may be compared with a standard to determine whether a sediment zone needs to be removed or to determine whether the sediment has been sufficiently remediated.

Pre-remediation calculation of the area-concentration of the sediment zones may be used to determine whether it is worthwhile to remove the sediment. Furthermore, post-remediation calculation of the area-concentration may be used to determine whether the remediation was effective.

For example, the area-concentrations of contiguous sediment zones may be collected together to give a surface weighted average concentration (SWAC) for a particular section or reach of the water course. Comparing the pre- and post-remediation SWACs is one method of determining or projecting the effectiveness of a remediation project for that reach.

The SWAC is calculated by dividing the summed area-concentrations for sediment zones in a reach by the summed area of the zones in the reach as represented in the following formula: $\Sigma PA/\Sigma A$.

Some or all of the steps of the methods discussed herein may be carried out or implemented with a computer system. The computer system may include suitable computer executable instructions to carry out any and all the functionality that may be required or desirable to carry out the steps of the disclosed methods or to operate the disclosed systems. The computer system may include computer-executable instructions, computer-readable media, and communication media. Computer-executable instructions (e.g. software and software updates), such as program modules (e.g. routines, programs, objects, components, data structures, and so forth), may be executed by one or more computers or other devices and perform particular tasks or implement particular abstract data types. Computer-executable instructions, such as program modules, may be implemented on, or associated with, various computer-readable media. Communication media typically embody computer-executable instructions, in a modulated data signal such as a carrier wave or other transport mechanism and include any information delivery media. By way of example, and not limitation, communication media include wired media such as a wired network or direct-wired connection, and wireless media such as acoustic, RF infrared, infrared, and the like. Combinations of any of the above should also be included with the scope of computer-readable media.

The present method and systems are suitable for a wide variety of contaminants including polychlorinated bipenyls, pesticides, polynuclear aromatic hydrocarbons, petroleum hydrocarbons, metals, or any other organic, inorganic or organometallic chemical compound which, by one mechanism or another, may become associated with sediments.

For example the contaminant may include one or more compounds from the following classes: acrylamides, acrylic acids and its esters, aldehydes, aliphatic imines, alkanolamines, alkenes, alkylbenzenes, aluminum and its compounds, aminoazobenzenes, azobenzenes, antimony and its compounds, arsenic and its compounds, aryl sulfonic acids and salts, aryl phosphates, azides, inorganic, benzenepolycarboxylates, benzotriazoles, beryllium and its compounds, biphenyl oxides, boron and its compounds, brominated dibenzo-p-dioxins, brominated diphenyl ethers, brominated aromatic compounds, bromobenzenes, bromochloromethanes, cadmium and its compounds, chlorofluorocarbons, chlorofluoroethylenes, chlorinated dibenzofurans, chlorinated paraffins, chlorinated naphthalenes, chlorinated dibenzo-p-dioxins, chlorinated benzenes, chloropentadienes, chlorophenols, chloropropenes, chlorotoluene, chromium and its compounds, cobalt and its compounds, copper and its compounds, creosote, cyclic alkenes, cyclopentadienes, dinitrophenols, dinitrotoluenes, dinitrocresols, epoxides, ethylene oxide, propylene oxide, butylene oxide, ethyl fluorocarbons, fluorides, fluorocarbons, glycols, glycol ethers, glycidyl ethers, haloalcohols, haloethanes, haloethers, halomethanes, halons, haloethylenes, halounsaturated ethanes, hydrochlorofluorocarbons, iron and its compounds, indium and its compounds, inorganic chlorines, inorganic sulfur, ketonic solvents, lead and its compounds, lithium and its compounds, manganese and its compounds, metallocenes, mercaptans, mercaptobenzothiazoles, methacrylic acid and its esters, molybdenum and its compounds, methyl fluorocarbons, methyl ethyl benzene, nickel and its compounds, nitroparaffins, nitroaromatic compounds, nitriles, nicotine and salts, nitrobenzenes, nitroparaffins, nitrophenols, nitrotoluenes, organic acids, organic anhydrides, organic peroxides, organic silicon compounds, organoarsenicals, organoisocyanates, organolead compounds, organomercurials, organophosphate compounds, palladium and its compounds, pesticides, perfluorinated compounds (e.g. perfluorinated carbons), petroleum hydrocarbons, phthalates esters, platinum and its compounds, polychlorinated biphenols, polychlorinated biphenyls, polycyclic organic matter, polyethylene glycolspolynuclear aromatic hydrocarbons, polypropylene glycols, selenium and its compounds, silicones, siloxanes, silver and its compounds, tellurium and its compounds, tetramethylbenzenes, thallium and its compounds, thioureas, titanium and its compounds, trichlorobenzenes, trimethylbenzenes, trinitrophenols, uranium and its compound, xylenols, zinc and its compounds, and combinations thereof.

It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. Plural structural components or steps can be provided by a single integrated structure or step. Alternatively, a single integrated structure or step might be divided into separate plural components or steps. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

EXAMPLE

Table 1 shows the pre-remediation data for the overbank areas of the water course illustrated in FIG. 1. Each polygon number is labeled on FIG. 1, as is each sample ID. As can been seen from the table, for each polygon has a contaminant concentration an erosion factor, and a risk attenuation factor. From these, the adjusted contaminant concentration is calculated. With the area of the polygon, the area-concentration for each polygon is calculated. To determine the SWAC, the summed area-concentrations for the polygons is divided by the summed areas of the polygons. For this particular section of the water course, the pre-remediation SWAC is 0.35.

TABLE 1

| Polygon Number (sample #) | Sample ID | Conc. (ppm) | Erosion Factor | Erosion potential | Risk Attenuation Factor | Adjusted Concentration (ppm) | Area (sq. ft.) | PPM × Area (ppm × sq ft) |
|---|---|---|---|---|---|---|---|---|
| 1 (52) | P-FVD-SS-I5 | 2.23 | 0.1 | none | 1 | 0.220 | 803.710 | 179.23 |
| 2 (52) | P-FVD-SS-I5 | 2.23 | 0.25 | low | 1 | 0.560 | 958.940 | 534.61 |
| 3 (70) | I6 | 0.5 | 0.1 | none | 1 | 0.050 | 639.700 | 31.98 |
| 4 (6) | RA-56 + 90-E15 | 0.84 | 0.1 | none | 1 | 0.080 | 811.160 | 68.14 |
| 5 (3) | RA-52 + 20-E5 | 3.4 | 0.1 | none | 1 | 0.340 | 454.330 | 154.47 |
| 6 (4) | RA-53 + 30-W15 | 23 | 0.1 | none | 1 | 2.300 | 1,189.520 | 2,735.90 |
| 7 (70) | I6 | 0.5 | 1 | high | 1 | 0.500 | 2,080.630 | 1,040.31 |
| 8 (4) | RA-53 + 30-W15 | 23 | 0.25 | low | 1 | 5.750 | 1,020.140 | 5,865.79 |
| 9 (5) | RA-53 + 30-W30 | 8.2 | 0.1 | none | 1 | 0.820 | 1,232.590 | 1,010.72 |
| 10 (6) | RA-56 + 90-E15 | 0.84 | 0.5 | medium | 1 | 0.420 | 1,620.710 | 680.70 |
| 11 (6) | RA-56 + 90-E15 | 0.84 | 0.1 | none | 1 | 0.080 | 2,488.280 | 209.02 |
| 12 (6) | RA-56 + 90-E15 | 0.84 | 0.1 | none | 1 | 0.080 | 72,095.220 | 6,056.00 |
| 13 (6) | RA-56 + 90-E15 | 0.84 | 1 | high | 1 | 0.840 | 4,997.930 | 4,198.26 |
| 14 (6) | RA-56 + 90-E15 | 0.84 | 0.1 | none | 1 | 0.080 | 99,001.050 | 8,316.09 |
| 25 (4) | RA-53 + 30-W15 | 23 | 0.25 | low | 1 | 5.750 | 443.700 | 2,551.25 |
| 26 (9) | RA-58 + 65-W3 | 46 | 0.1 | none | 1 | 4.600 | 429.050 | 1,973.64 |
| 27 (12) | F5950-W11 | 9.1 | 0.1 | none | 1 | 0.910 | 8,950.510 | 8,144.96 |
| 28 (11) | F5950-E60 | 2.3 | 0.1 | none | 1 | 0.230 | 8,181.590 | 1,881.77 |
| 29 (12) | F5950-W11 | 9.1 | 0.1 | none | 1 | 0.910 | 1,599.910 | 1,455.92 |
| 30 (10) | RA-59 + 50-E15-RESAMPLE | 7.1 | 0.1 | none | 1 | 0.710 | 1,685.860 | 1,196.96 |
| 32 (6) | RA-56 + 90-E15 | 0.84 | 0.1 | none | 1 | 0.080 | 3,586.620 | 301.28 |
| 33 (10) | RA-59 + 50-E15-RESAMPLE | 7.1 | 0.25 | low | 1 | 1.780 | 2,319.050 | 4,116.32 |
| 34 (3) | RA-52 + 20-E5 | 3.4 | 0.25 | low | 1 | 0.850 | 464.250 | 394.62 |
| 48 (11) | F5950-E60 | 2.3 | 0.1 | none | 1 | 0.230 | 9,156.160 | 2,105.92 |
| 49 (11) | F5950-E60 | 2.3 | 0.1 | none | 1 | 0.230 | 1,644.120 | 378.15 |
| 50 (11) | F5950-E60 | 2.3 | 0.1 | none | 1 | 0.230 | 1,406.740 | 323.55 |
| 51 (11) | F5950-E60 | 2.3 | 0.1 | none | 1 | 0.230 | 39,192.850 | 9,014.36 |
| 188 (1) | RA-50 + 60-W10 | 130 | 0.25 | low | 1 | 32.500 | 599.900 | 19,496.78 |
| 189 (11) | RA-50 + 60-W10 | 130 | 0.5 | medium | 1 | 65.000 | 166.190 | 10,802.47 |
| | | | | | | Sum | 269,220.410 | 95,219.15 |
| | | | | | | SWAC | 0.35 | |

Figure 2:
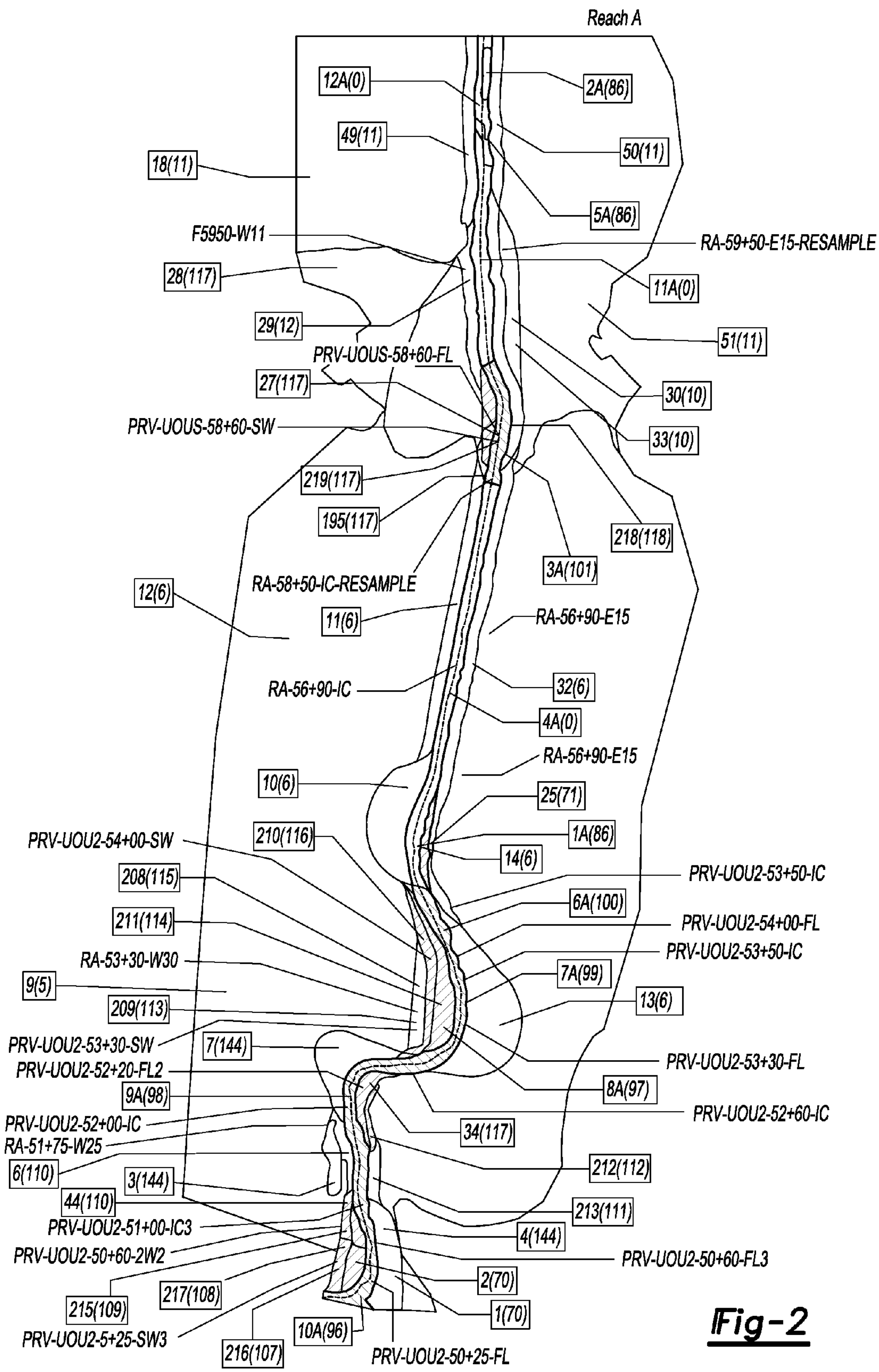
FIG. 2. depicts the remediation site in which post-remediation contaminant concentration have been calculated.

Table 2 shows post-remediation data for the overbank areas of the water course illustrated in FIG. 2. As in Table 1, each polygon number is labeled on FIG. 2, as is each sample ID.

TABLE 2

| Polygon Number (sample #) | Sample ID | Conc. (ppm) | Erosion Factor | Erosion potential | Risk Attenuation Factor | Adjusted Concentration (ppm) | Area (sq. ft.) | PPM × Area (ppm × sq ft) |
|---|---|---|---|---|---|---|---|---|
| 1 (70) | I6 | 0.5 | 0.1 | very low | 1 | 0.050 | 803.710 | 40.19 |
| 2 (70) | I6 | 0.5 | 0.25 | low | 1 | 0.125 | 958.940 | 119.87 |

TABLE 2-continued

| Polygon Number (sample #) | Sample ID | Conc. (ppm) | Erosion Factor | Erosion potential | Risk Attenuation Factor | Adjusted Concentration (ppm) | Area (sq. ft.) | PPM × Area (ppm × sq ft) |
|---|---|---|---|---|---|---|---|---|
| 3 (144) | RA-51 + 75-W25 | 2.1 | 0.1 | very low | 1 | 0.210 | 639.700 | 134.31 |
| 4 (144) | RA-51 + 75-W25 | 2.1 | 0.1 | very low | 1 | 0.210 | 491.830 | 103.28 |
| 6 (110) | PRV-UOU2-50 + 60-SW2 | 0.03 | 0.1 | very low | 1 | 0.003 | 564.240 | 1.69 |
| 7 (144) | RA-51 + 75-W25 | 2.1 | 0.5 | medium | 1 | 1.050 | 2,027.730 | 2,129.12 |
| 9 (5) | RA-53 + 30-W30 | 8.2 | 0.1 | very low | 1 | 0.820 | 927.390 | 760.46 |
| 10 (6) | RA-56 + 90-E15 | 0.84 | 0.5 | medium | 1 | 0.420 | 3,136.950 | 1,317.52 |
| 11 (6) | RA-56 + 90-E15 | 0.84 | 0.1 | very low | 1 | 0.084 | 2,488.280 | 209.02 |
| 12 (6) | RA-56 + 90-E15 | 0.84 | 0.1 | very low | 1 | 0.084 | 106,290.320 | 8,928.39 |
| 13 (6) | RA-56 + 90-E15 | 0.84 | 0.5 | medium | 1 | 0.420 | 4,997.930 | 2,099.13 |
| 14 (6) | RA-56 + 90-E15 | 0.84 | 0.1 | very low | 1 | 0.084 | 98,893.270 | 8,307.03 |
| 25 (71) | RA-54 + 90-ES | 5.5 | 0.25 | low | 1 | 1.375 | 443.700 | 610.08 |
| 27 (117) | PRV-UOU2-58 + 60-SW | 0.005 | 0.1 | very low | 1 | 0.001 | 8,926.570 | 4.46 |
| 28 (117) | PRV-UOU2-58 + 60-SW | 0.005 | 0.1 | very low | 1 | 0.001 | 8,181.590 | 4.09 |
| 29 (12) | F5950-W11 | 9.1 | 0.1 | very low | 1 | 0.910 | 1,213.280 | 1,104.08 |
| 30 (10) | RA-59 + 50-E15-RESAMPLE | 7.1 | 0.1 | very low | 1 | 0.710 | 1,685.860 | 1,196.96 |
| 32 (6) | RA-56 + 90-E15 | 0.84 | 0.1 | very low | 1 | 0.084 | 3,586.620 | 301.28 |
| 33 (10) | RA-59 + 50-E15-RESAMPLE | 7.1 | 0.25 | low | 1 | 1.775 | 2,319.050 | 4,116.32 |
| 34 (117) | PRV-UOU2-52 + 20-SW2 | 2.9 | 0.25 | low | 1 | 0.725 | 463.940 | 336.36 |
| 48 (11) | F5950-E60 | 2.3 | 0.1 | very low | 1 | 0.230 | 26,954.490 | 6,199.53 |
| 49 (11) | F5950-E60 | 2.3 | 0.1 | very low | 1 | 0.230 | 1,644.120 | 378.15 |
| 50 (11) | F5950-E60 | 2.3 | 0.1 | very low | 1 | 0.230 | 1,406.740 | 323.55 |
| 51 (11) | F5950-E60 | 2.3 | 0.1 | very low | 1 | 0.230 | 39,192.860 | 9,014.36 |
| 195 (117) | PRV-UOU2-58 + 60-SW | 0.005 | 0.1 | very low | 1 | 0.001 | 113.530 | 0.06 |
| 208 (115) | PRV-UOU2-54 + 00-SW | 0.03 | 0.1 | very low | 1 | 0.003 | 648.670 | 1.95 |
| 209 (113) | PRV-UOU2-53 + 30-SW | 0.26 | 0.1 | very low | 1 | 0.026 | 479.370 | 12.46 |
| 213 (111) | PRV-UOU2-52 + 20-SW2 | 2.9 | 0.1 | very low | 1 | 0.290 | 250.710 | 72.70 |
| 214 (110) | PRV-UOU2-50 + 60-SW2 | 0.03 | 0.1 | very low | 1 | 0.003 | 302.500 | 0.91 |
| 217 (108) | PRV-UOU2-50 + 25-SW3 | 4.8 | 0.1 | very low | 1 | 0.480 | 481.710 | 231.22 |
| 219 (117) | PRV-UOU2-58 + 60-SW | 0.005 | 0.1 | very low | 1 | 0.001 | 354.880 | 0.18 |
| | | | | | | Sum | 320,870.47 | 48,058.73 |
| | | | | | | SWAC | .015 | |

For this particular section of the overbank areas of the water course, the post-remediation SWAC is 0.15, thus indicating an improvement (i.e. reduction) in the amount of contaminant in the section of water course.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method comprising:

identifying one or more sediment zones of a watercourse as erosion or deposition zones of a watercourse;

assigning an erosion factor for each sediment zone based on the identifying step;

assigning a risk attenuation factor for each sediment zone based on the identifying step;

assigning an estimated contaminant concentration for at least one sediment zone based on one or more proxy sediment zones; and calculating an adjusted contaminant concentration for each sediment zones in a site containing a water course, comprising multiplying a known or estimated contaminant concentration by the erosion factor and by the risk attenuation factor, wherein the calculating step is implemented in a computer.

2. The method of claim 1 further comprising identifying erosion or deposition zones through the application of geomorphological principals.

3. The method of claim 2 wherein identifying erosion or deposition zones comprises comparing images of the site that are separated in time, analyzing topographical features of the site, or combinations thereof.

4. The method of claim 3 wherein identifying erosion or deposition zones further comprises using images, topographical data, visual inspections, sediment identification, soil profiles or combinations thereof.

5. The method of claim 1 further comprising calculating the area-concentration of each sediment zone by multiplying the adjusted concentration of each sediment zone by the area of each sediment zone.

6. The method of claim 1 further comprising calculating a surface weighted average concentration for a section of the water course.

7. The method of claim 1 further comprising remediating one or more sediment zones where the adjusted contaminant concentration is above a standard.

8. The method of claim 1 further comprising assigning the estimated contaminant concentration for each sediment zone by using a known contaminant concentration of one or more different sediment zones, and wherein the calculating step comprising multiplying the estimated contaminant concentration by the erosion factor and by the risk attenuation factor.

9. The method of claim 8 wherein each sediment zones with the estimated contaminant concentration and the one or more sediment zones with known contaminant concentrations have one or more of following characteristics: i) similar sediment type; ii) similar relationship to the water course; or iii) similar location within the water course.

10. A method for determining the selective removal of sediment containing a contaminant, comprising:

identifying one or more sediment zones of a water course in a site by comparing images of the site that are separated in time, analyzing topographical features of the site, or by using images, topographical data, visual inspections, sediment identification, soil profiles or combinations thereof to determine the location of deposition and erosion zones within the water course;

assigning an erosion factor for each sediment zone based on the identifying step;

assigning a risk attenuation factor for each sediment zone based on the identifying step;

assigning an estimated contaminant concentration for at least one sediment zone based on one or more proxy sediment zones; and calculating an adjusting adjusted contaminant concentration for each sediment zone, comprising multiplying a known or estimated contaminant concentration by the erosion factor and by the risk attenuation factor; wherein the calculating step is implemented in a computer;

determining whether each sediment zone is in need of remediation by comparison of the adjusted contaminant concentration to a standard; and designing a remediation plan based on the determination of which of the sediment zones are in need of remediation.

11. The method of claim 10 further comprising implementing the designed remediation plan.

12. The method of claim 11 further comprising verifying the implantation of the remediation plan.

13. The method of claim 12 wherein the verifying step comprises post-remediation sediment sampling, calculating a post-remediation adjusted contaminant concentration for the one or more sediment zones that have been remediated, or combinations thereof.

14. The method of claim 10 further comprising calculating the area-concentration of each sediment zone by multiplying the adjusted concentration and the area of each sediment zone.

15. The method claim 10 further comprising calculating a surface weighted average concentration for at least one section of the water course before designing the remediation plan.

16. The method of claim 12 wherein the verifying step comprises post-remediation sediment sampling, calculating a post-remediation adjusted contaminant concentration for the one or more sediment zones that have been remediated, calculating a post-remediation surface weighted average concentration for the section of the watercourse that has been remediated, or combinations thereof.

17. The method of claim 10 further comprising assigning the estimated contaminant concentration for each sediment zone by using a known contaminant concentration of one or more different sediment zones, wherein each sediment zone with the estimated contaminant concentration and the one or more sediment zones with known contaminant concentrations have one or more of following characteristics: i) similar sediment type; ii) similar relationship to the water course; or iii) similar location within the water course, and wherein the calculating step comprising multiplying the estimated contaminant concentration by the erosion factor and by the risk attenuation factor.

18. A method for selective removal of sediment containing a contaminant, comprising:

after ongoing contamination of a contaminant has been eliminated, identifying one or more sediment zones of a water course in a site to determine the location of deposition and erosion zones within the water course;

assigning an erosion factor for each sediment zone based on the identifying step;

assigning a risk attenuation factor for each sediment zone based on the identifying step;

assigning an estimated contaminant concentration for at least one sediment zone based on one or more proxy sediment zones;

calculating an adjusted contaminant concentration for each sediment zones site, comprising multiplying the estimated contaminant concentration by the erosion factor and by the reintroduction risk attenuation factor, wherein the multiplying step is performed using a computer.

19. The method of claim 18 wherein the assigned estimated contaminant concentration is based on one or more similarities between each sediment zone and the one or more proxy sediment zones, wherein the similarities include: i) sediment type; ii) relationship to the water course; or iii) location with the water course.

20. The method of claim 19 wherein the identification step comprises using images, topographical data, visual inspections, sediment identification, soil profiles and combinations thereof.

* * * * *